United States Patent [19]

Azzam

[11] Patent Number: 4,681,450
[45] Date of Patent: Jul. 21, 1987

[54] PHOTODETECTOR ARRANGEMENT FOR MEASURING THE STATE OF POLARIZATION OF LIGHT

[75] Inventor: Rasheed M. A. Azzam, New Orleans, La.

[73] Assignee: Research Corporation, New York, N.Y.

[21] Appl. No.: 747,611

[22] Filed: Jun. 21, 1985

[51] Int. Cl.[4] ............................................. G01J 4/04
[52] U.S. Cl. .................................. 356/367; 250/225; 356/369
[58] Field of Search .................. 356/351, 367, 369; 250/225

[56] References Cited

U.S. PATENT DOCUMENTS

| | | |
|---|---|---|
| 2,412,074 | 12/1946 | Benford . |
| 2,583,186 | 1/1952 | Mueller . |
| 2,986,066 | 5/1961 | Rouy . |
| 3,001,439 | 9/1961 | Rouy . |
| 3,283,645 | 11/1966 | Wada . |
| 3,506,835 | 4/1970 | Foster .......................... 356/351 X |
| 3,623,814 | 11/1971 | Buhrer . |
| 3,631,254 | 12/1971 | Covault . |
| 3,642,375 | 2/1972 | Macek . |
| 3,728,030 | 4/1973 | Hawes . |
| 4,118,125 | 10/1978 | Gundermann . |
| 4,158,506 | 6/1979 | Collet . |
| 4,203,670 | 5/1980 | Bromberg . |
| 4,306,809 | 12/1981 | Azzam . |
| 4,309,110 | 1/1982 | Tumerman . |
| 4,323,899 | 4/1982 | Barnes et al. . |
| 4,332,476 | 6/1982 | Stenberg et al. . |
| 4,333,008 | 6/1982 | Misek . |
| 4,335,939 | 6/1982 | Stovell et al. . |
| 4,392,722 | 7/1983 | Shirasaki . |

OTHER PUBLICATIONS

Optica Acta, 1982, vol. 29, No. 5, pp. 685-689, Journal of Physics E Scientific Instruments, vol. 9., No. 7, issued Jul. 1976.

*Primary Examiner*—Davis L. Willis
*Assistant Examiner*—Matthew W. Koren
*Attorney, Agent, or Firm*—Scully, Scott, Murphy & Presser

[57] ABSTRACT

A photopolarimeter for the simultaneous measurement of all four Stokes parameters of light. The light beam, the state of polarization of which is to be determined, strikes, at oblique angles of incidence, three photodetector surfaces in succession, each of which is partially specularly reflecting and each of which generates an electrical signal proportional to the fraction of the radiation it absorbs. A fourth photodetector is substantially totally light absorbtive and detects the remainder of the light. The four outputs thus developed form a 4x1 signal vector $\bar{I}$ which is linearly related, $\bar{I} = \bar{A}\,\bar{S}$, to the input Stokes vector $\bar{S}$. Consequently, $\bar{S}$ is obtained by $\bar{S} = \bar{A}^{-1}\bar{I}$. The 4x4 instrument matrix $\bar{A}$ must be nonsingular, which requires that the planes of incidence for the first three detector surfaces are all different. For a given arrangement of four detectors, $\bar{A}$ can be either computed or determined by calibration.

10 Claims, 2 Drawing Figures

PHOTODETECTOR ARRANGEMENT FOR MEASURING THE STATE OF POLARIZATION OF LIGHT

BACKGROUND OF THE INVENTION

1. Field of the Invention

The present invention relates generally to a relatively simple photopolarimeter and method for measuring the state of polarization of a light beam, and more particularly pertains to a unique and simple photopolarimeter and method for simultaneously measuring all four Stokes parameters defining the state of polarization of a light beam which does not require any of the usual prior art polarizing elements such as wave retarders and polarizers.

2. Discussion of the Prior Art

The most general state of partial polarization of a light beam is conveniently described by the four Stokes parameters (see, for example, M. Born and E. Wolf, *Principles of Optics* (Pergamon, New York, 1975), p. 554). A large number of photopolarimeters dedicated to the measurement of the Stokes parameters has been introduced, and an excellent review thereof is given by P. S. Hauge, *Surface Sci.* 96, 108 (1980), and by K. Serkowski, in *Planet, Stars and Nebulae Studied with Photopolarimetry* (University of Arizona Press, Tucson, 1977), pp. 135-174.

Usually the light beam is passed through a sequence of optical elements (analyzing optics that consist of linear retarders, rotators and polarizers), and the emergent light flux is measured by linear photodetection. Flux measurements can be repeated for different (at least four) discrete settings of the analyzing optics, or alternatively, continuous periodic modulation is applied to one or more optical elements and the detected signal is Fourier analyzed to determine the four Stokes parameters (R. M. A. Azzam, *Optik* 52, 253 (1979)). Other prior art techniques for the simultaneous measurement of all four Stokes parameters employ division of wavefront (E. Collett, *Surface Sci.* 96, 156 (1980)) and division of amplitude (R. M. A. Azzam, *Optica Acta* 29, 685 1982)). All of the previously described photopolarimeters require polarizing optical elements such as wave retarders and polarizers.

SUMMARY OF THE INVENTION

Accordingly, it is a primary object of the present invention to provide a relatively simple photopolarimeter and method for measuring the state of polarization of a light beam.

A further object of the subject invention is the provision of a photopolarimeter and method for simultaneously measuring all four Stokes parameters defining the state of polarization of a light beam which does not require any of the usual prior art polarizing elements such as wave retarders and polarizers.

In accordance with the teachings herein, the present invention provides a photopolarimeter and method in which the light beam is incident on a first photodetector having a partially specularly reflecting surface at an oblique angle with a first plane of incidence, and is partially reflected therefrom. The first photodetector produces a first electrical output signal having a magnitude proportional to the radiation absorbed thereby.

The light beam partially reflected from the first photodetector is reflected onto a second photodetector also having a partially specularly reflecting surface. The second photodetector is positioned such that the light beam is incident thereon at an oblique angle with a second plane of incidence, different from the first plane of incidence, and is partially reflected therefrom. The second photodetector also produces a second electrical output signal having a magnitude proportional to the radiation absorbed thereby.

The light beam partially reflected from the second photodetector is reflected onto a third photodetector also having a partially specularly reflecting surface. The third photodetector is positioned such that the light beam is incident thereon at an oblique angle with a third plane of incidence, different from the second plane of incidence, and is partially reflected therefrom. The third photodetector also produces a third electrical output signal having a magnitude proportional to the radiation absorbed thereby.

The light beam partially reflected from the third photodetector is reflected onto a fourth photodetector having a substantially totally light absorptive surface. The fourth photodetector produces a fourth electrical output signal having a magnitude proportional to the radiation absorbed thereby.

In greater particularity, the first, second, third and fourth output signals are utilized to simultaneously measure all four Stokes parameters defining the state of polarization of a light beam. This is accomplished by first determining $\overline{A}$, a four by four photopolarimeter matrix, converting each of the first, second, third and fourth output signals to a corresponding digital signal, and calculating each of the four Stokes parameters pursuant to $\overline{S} = \overline{A}^{-1} \overline{I}$, wherein $\overline{A}$ is the four by four photopolarimeter matrix, and $\overline{I}$ is a four by one signal vector comprising said first, second, third and fourth output signals. A microcomputer is preferably employed to perform the calculation $\overline{S} = \overline{A}^{-1} \overline{I}$, and $\overline{A}$ or $\overline{A}^{-1}$ is stored in the memory of the microcomputer. $\overline{A}$ is preferably determined by calibrating the arrangement of the four photodetectors, which includes illuminating the photopolarimeter with input light that is polarized, sequentially, in four different linearly independent states, represented by four known linearly independent Stokes vectors, and recording the corresponding signal vector for each input state to determine $\overline{A}$. $\overline{A}$ can also be determined by a calculation by utilizing the Mueller matrix $\overline{M}$ and the rotation matrix $\overline{R}$.

The polarimeter and method of the present invention have the following advantages relative to prior art polarimeters:

(1) The present invention is a complete polarimeter that determines all four Stokes parameters, and hence the most general state of (partial elliptical) polarization.

(2) All four Stokes parameters are determined simultaneously (not sequentially).

(3) No separate polarizing optical elements (e.g. sheet or crystal polarizers or quarterwave plates) are needed, in effect, the partially reflecting surfaces of the photodetectors ($D_0$, $D_1$ and $D_2$ in FIG. 1) perform these functions.

(4) The instrument has no moving parts, in contrast with prior art photopolarimeters that use synchronously rotatin optical elements (D. E. Aspnes and P. S. Hauge, *J. Opt. Soc. Am.* 66, 949 (1976)).

(5) No modulators, such as the often used photoelastic device (see, for example, R. J. Perry, A. H. Hunt and D. R. Huffman, *Appl. Opt.* 17, 2700 (1978)) are required either.

(6) The subject invention provides a rugged design consisting of four solid-state photodetectors.

(7) The present invention provides efficient and complete utilization of the input light flux (which is shared by the four photodetectors) for the polarization determination.

(8) Several built-in degrees of freedom are provided that can be varied to achieve optimal performance, including the geometrical arrangement of the four detectors (angles of incidence, angles between successive planes of incidence), the surface reflection parameters $(r, \psi, \Delta)$ of each detector which can be greatly modified by dielectric thin-film coatings, and the photoelectric response factors and postdetection gains ($k_0$, $k_1$, $k_2$ and $k_3$).

(9) The instrument can be readily interfaced to an on-line microcomputer which receives as its input the digitized output electrical signals $i_0$, $i_1$, $i_2$ and $i_3$. The microcomputer stores the instrument matrix $\overline{A}$, determines its inverse, and calculates the four Stokes parameters. The result can be displayed on a suitable output device.

BRIEF DESCRIPTION OF THE DRAWINGS

The foregoing objects and advantages of the present invention for a photodetector arrangement for measuring the state of polarization of light may be more readily understood by one skilled in the art with reference being had to the following detailed description of a preferred embodiment thereof, taken in conjunction with the accompanying drawings wherein like elements are designated by identical reference numerals throughout the several views, and in which.

DETAILED DESCRIPTION OF THE DRAWINGS

Figure 1:
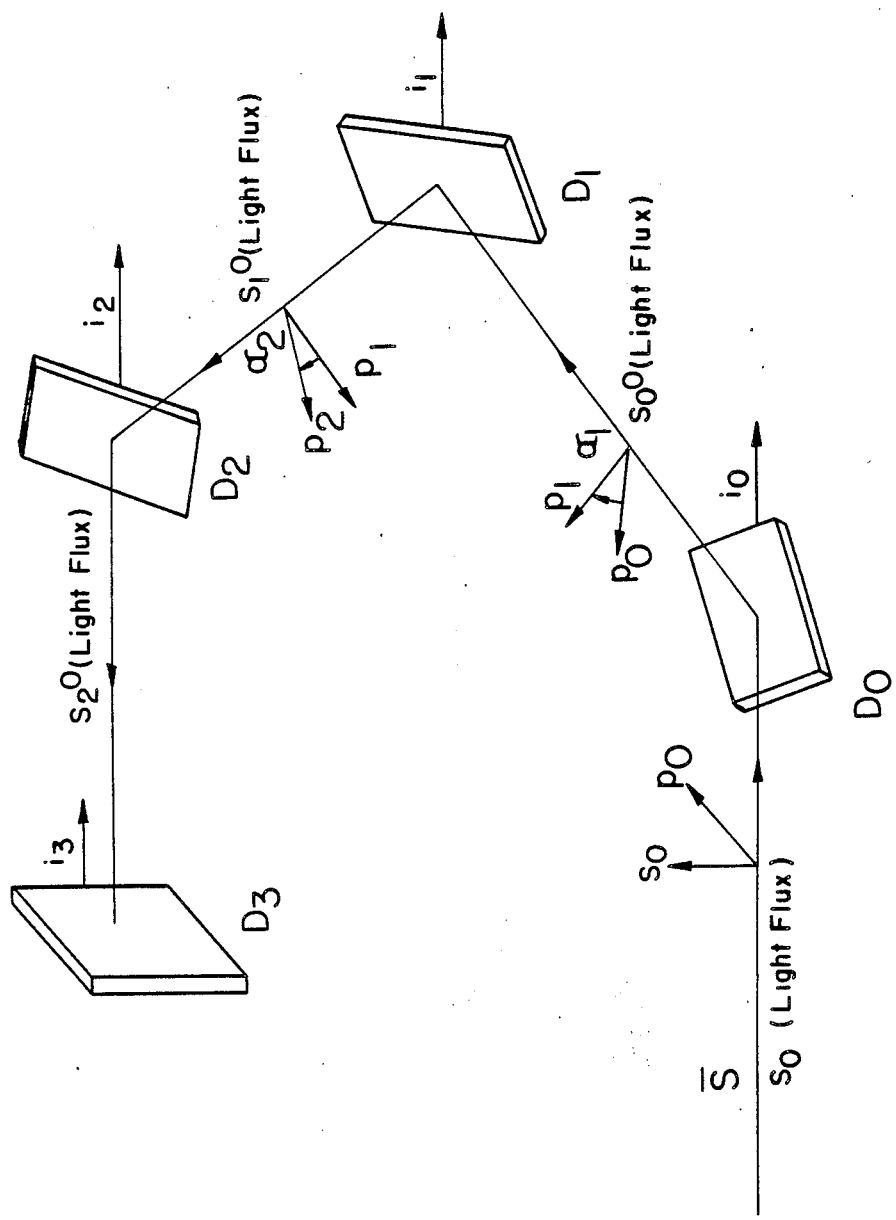
FIG. 1 is a schematic diagram of an exemplary embodiment of a photopolarimeter constructed pursuant to the teachings of the present invention.

Referring to the drawings in detail, FIG. 1 illustrates a schematic diagram of the proposed photopolarimeter which is an arrangement of four photodetectors $D_0$, $D_1$, $D_2$, and $D_3$. The surfaces of $D_0$, $D_1$, and $D_2$ are obliquely partially specularly reflecting, whereas the surface of $D_3$ is substantially totally light absorbtive (i.e. achieved by anti-reflection coatings) for the light that falls (normally) thereon. Each photodetector $D_m$ generates an output electrical signal $i_m$ ($m=0, 1, 2, 3$) that is proportional to the light flux that it absorbs.

As is well recognized in the art, the plane of incidence for an input light beam is defined by a line perpendicular to the plane of the surface (partially reflective specular surface of the detector) and the direction of propagation of the incident light beam.

As is also well recognized in the art, whenever light is reflected from an uncoated polished surface, a much larger part of the reflected beam is vibrating at right angles to the plane of incidence than in that plane. The amount of polarization produced by reflection from the polished surface is also directly related to the angle of incidence of the light on the surface. Accordingly, the light absorbed and detected by the detector $D_0$ (and also $D_1$ and $D_2$) is directly related to the state of polarization of the incident light beam and its angle of incidence relative to the surface of detector $D_0$.

If the Stokes vector of the incident (or input) light to be measured is denoted by:

$$\overline{S} = \begin{bmatrix} S_0 \\ S_1 \\ S_2 \\ S_3 \end{bmatrix}, \quad (1)$$

the Stokes vectors of the light reflected from the surfaces of photodetectors $D_0$, $D_1$, and $D_2$ are given by:

$$\overline{S}_0 = \overline{M}_0 \overline{S}, \quad (2)$$
$$\overline{S}_1 = \overline{M}_1 \overline{R}_1 (\alpha_1) \overline{M}_0 \overline{S},$$
$$\overline{S}_2 = \overline{M}_2 \overline{R}_2 (\alpha_2) \overline{M}_1 \overline{R}_1 (\alpha_1) \overline{M}_0 \overline{S},$$

respectively. For a discussion of the Mueller-matrix calculus see, for example, W. A. Shurcliff, *Polarized Light* (Harvard University Press, Cambridge, 1962), Chap. 8. $\overline{S}_n$ ($n=0, 1, 2$) is defined with respect to the orthogonal directions parallel ($p_n$) and perpendicular ($s_n$) to the plane of incidence for reflection from the $n^{th}$ detector. ($\overline{S}$ is defined with respect to the orthogonal axes $p_0$, $s_0$.) The effect of reflection on the state of polarization is described by the Mueller matrix $\overline{M}_n$ which is referenced to the $p_n$, $s_n$ coordinate system. In Eqs. (2), the 4×4 Mueller rotation matrices $\overline{R}_1 (\alpha_1)$ and $\overline{R}_2 (\alpha_2)$ account for rotations of the plane of incidence in going from one reflection to the next. As illustrated in FIG. 1, $\alpha_1$ is the angle between the directions $p_1$ and $p_0$ and, likewise, $\alpha_2$ is the angle between the directions $p_2$ and $p_1$.

The light flux of the beam along its segmented path is given by $S_0$, $S_0^0$, $S_1^0$, and $S_2^0$ which are the first elements of the Stokes vectors $\overline{S}$, $\overline{S}_0$, $\overline{S}_1$, and $\overline{S}_2$, respectively. The electrical output signal of the $n^{th}$ detector is proportional to the light flux it absorbs, so that $$i_0 = k_0(S_0 - S_0^0), \quad (3)$$
$$i_1 = k_1(S_0^0 - S_1^0),$$
$$i_2 = k_2(S_1^0 - S_2^0),$$
$$i_3 = k_3 S_2^0.$$

The proportionality constant $k_n$ is a characteristic of the detector $D_n$ and includes any postdetection amplification factor. From Eqs. (1)–(3) it becomes apparent that each of the four output signals $i_0$, $i_1$, $i_3$ is a linear combination of the four Stokes parameters $S_0$, $S_1$, $S_2$ and $S_3$ of the input light. Therefore, we can write $$\begin{bmatrix} i_0 \\ i_1 \\ i_2 \\ i_3 \end{bmatrix} = \begin{bmatrix} a_{00} & a_{01} & a_{02} & a_{03} \\ a_{10} & a_{11} & a_{12} & a_{13} \\ a_{20} & a_{21} & a_{22} & a_{23} \\ a_{30} & a_{31} & a_{32} & a_{33} \end{bmatrix} \begin{bmatrix} S_0 \\ S_1 \\ S_2 \\ S_3 \end{bmatrix}, \quad (4)$$

or, more compactly, $$\overline{I} = \overline{A}\overline{S}. \quad (5)$$

$\overline{I}$ is the 4×1 signal vector that appears on the left-hand side of Eq. (4) and $\overline{A}$ is the 4×4 instrument matrix of real numbers that appears on the right-hand side. Matrix inversion produces $$\overline{S} = \overline{A}^{-1} \overline{I}, \quad (6)$$

from Eq. (5). Equation (6) indicates how the unknown Stokes vector $\bar{S}$ of the input light can be obtained from the signal vector $\bar{I}$ and the instrument matrix $\bar{A}$. Of course $\bar{A}$ must be nonsingular, a condition that requires that the light beam does not remain in one plane (i.e. the plane of incidence for a given reflection must be rotated with respect to that of the preceding planes of incidence).

The instrument matrix $\bar{A}$ can be calculated from the arrangement and characteristics of the four photodetectors. If the p and s linear polarizations (parallel and perpendicular to the plane of incidence) are the eigenpolarizations of reflection, the Mueller matrix $\bar{M}$ is given by (R. M. A. Azzam and N. M. Bashara, *Ellipsometry and Polarized Light* (North Holland, Amsterdam, 1977), pp. 491-2):

$$\bar{M} = r \begin{bmatrix} 1 & -\cos 2\psi & 0 & 0 \\ -\cos 2\psi & 1 & 0 & 0 \\ 0 & 0 & \sin 2\psi \cos\Delta & \sin 2\psi \sin\Delta \\ 0 & 0 & -\sin 2\psi \sin\Delta & \sin 2\psi \cos\Delta \end{bmatrix}, \quad (7)$$

where r is the intensity reflectance for unpolarized (or circularly polarized) incident light, and $\tan\psi \exp(j\Delta)$ is the ratio of the complex p and s reflection coefficients. The rotation matrix is given by (R. M. A. Azzam and N. M. Bashara, *Ellipsometry and Polarized Light* (North Holland, Amsterdam, 1977), pp. 491-2):

$$\bar{R}(\alpha)) = \begin{bmatrix} 1 & 0 & 0 & 0 \\ 0 & \cos 2\alpha & \sin 2\alpha & 0 \\ 0 & -\sin 2\alpha & \cos 2\alpha & 0 \\ 0 & 0 & 0 & 1 \end{bmatrix}. \quad (8)$$

Combining Eqs. (7) and (8) into Esq. (1)-(3) enables the explicit exposition of the individual elements $a_{mn}$ of the matrix $\bar{A}$. The results for the general case, when $r, \psi, \Delta$ are arbitrary and differ from one detector to the other and the rotations $\alpha_1, \alpha_2$ are unequal, are too involved to be fully treated herein. For purposes of illustration, consider the special case of identical reflection parameters $r, \psi, \Delta$ for all of the first three detectors, and further assume that $\Delta = 90°$, which is always possible by choosing the angle of incidence to be equal to the principal angle (R. M. A. Azzam and A. R. M. Zaghloul, *J. Opt. Soc. Am.* 67, 1058 (1977); R. M. A. Azzam, *J. Opt. Soc. Am.* 71, 1523 (1981)). By setting $\Delta = 90°$ in Eq. (7), a simpler Mueller matrix $\bar{M}$ is obtained. Choosing $\alpha_1 = \alpha_2 = 45°$ also simplifies the rotation matrix $\bar{R}(\alpha)$ of Eq. (8). Substitution of these reduced matrices in Eqs. (1)-(3) gives the following instrument matrix $$\bar{A} = \begin{bmatrix} k_0 t & -k_0 r b & 0 & 0 \\ k_1 r t & k_1 r t b & 0 & -k_1 r^2 ab \\ k_2 r^2 t & k_2 r^2 t b & k_2 r^3 a^2 b & k_2 r^2 t ab \\ k_3 r^3 & k_3 r^3 b & -k_3 r^3 a^2 b & k_3 r^3 ab \end{bmatrix}, \quad (9)$$

where $$t = 1 - r, \quad a = \sin 2\psi, \quad b = -\cos 2\psi = -(1-a^2)^{\frac{1}{2}}. \quad (10)$$

It is essential that $\bar{A}$ of Eq. (9) be nonsingular. The determinant of $\bar{A}$ is given by $$\det\bar{A} = (k_0 k_1 k_2 k_3) r^4 a^3 b (1 - a^2 r), \quad (11)$$

which is not zero provided that $\psi \neq 0, \pi/4,$ or $\pi/2$.

Whereas the instrument matrix $\bar{A}$ can be calculated, as has already been demonstrated hereinabove, a more practical approach is to determine $\bar{A}$ by calibration for a given arrangement of four photodetectors. In this step, the instrument is illuminated with input light that is polarized, sequentially, in four different linearly independent states (represented by four known linearly independent Stokes vectors) and the corresponding signal vector is recorded for each input state. This data is sufficient to specify $\bar{A}$ completely through Eq. (4), and the polarimeter can then be utilized to determine any unknown input polarization state. It should be noted that $\bar{A}$ is a function of the wavelength of light and should be determined over the spectral range of interest. Monochromatic polarimeters are adequate in applications where the light originates from one of the more common types of lasers such as the 632.8-nm He-Ne laser or the 10.6. $\mu$m $CO_2$ laser.

The polarimeter and method described herein has the following advantages relative to prior art polarimeters:

(1) The present invention is a complete polarimeter that determines all four Stokes parameters, and hence the most general state of (partial elliptical) polarization.

(2) All four Stokes parameters are determined simultaneously (not one at a time).

(3) No separate polarizing optical elements (e.g. sheet or crystal polarizers or quarterwave plates) are needed; in effect, the partially reflecting surfaces of the photodetectors ($D_0$, $D_1$ and $D_2$ in FIG. 1) perform such function.

(4) The instrument has no moving parts, in contrast with prior art photopolarimeters that use synchronously rotating optical elements (D. E. Aspnes and P. S. Hauge, *J. Opt. Soc. Am.* 66, 949 (1976)).

(5) No modulators, such as the often used photoelastic device (see, for example, R. J. Perry, A. H. Hunt and D. R. Huffman, *Appl. Opt.* 17, 2700 (1978)) are required either.

(6) The subject invention provides a rugged design that consists of four solid-state photodetectors.

(7) The present invention provides efficient and complete utilization of the input light flux (which is shared by the four photodetectors) for the polarization determination.

(8) Several built-in degrees of freedom are provided that can be varied to achieve optimal performance, including the geometrical arrangement of the four detectors (angles of incidence, angles between successive planes of incidence), the surface reflection parameters ($r, \psi, \Delta$) of each detector which can be greatly modified by dielectric thin-film coatings, and the photoelectric response factors and postdetection gains ($k_0$, $k_1$, $k_2$ and $k_3$).

(9) The instrument can be readily interfaced to an on-line microcomputer which receives as its input the digitized output electrical signals $i_0$, $i_1$, $i_2$ and $i_3$. The microcomputer stores the instrument matrix $\bar{A}$, determines its inverse, and calculates the four Stokes parameters using Eq. (6). The result can be displayed on a suitable output device.

In summary, in the four-detector photopolarimeter of FIG. 1, the surfaces of photodetectors $D_0$, $D_1$ and $D_2$ are partially specularly reflecting, whereas that of $D_3$ is substantially totally absorbing. The four output electrical signals $i_0$, $i_1$, $i_2$ and $i_3$ are utilized to determine the input Stokes vector $\bar{S}$. $\alpha_1$ is the angle between the planes of incidence for the successive reflections from $D_0$ and $D_1$, $\alpha_2$ is the corresponding angle for the reflections from $D_1$ and $D_2$, and $p_n$ is the reference polarization direction parallel to the $n^{th}$ plane of incidence.

Figure 2:
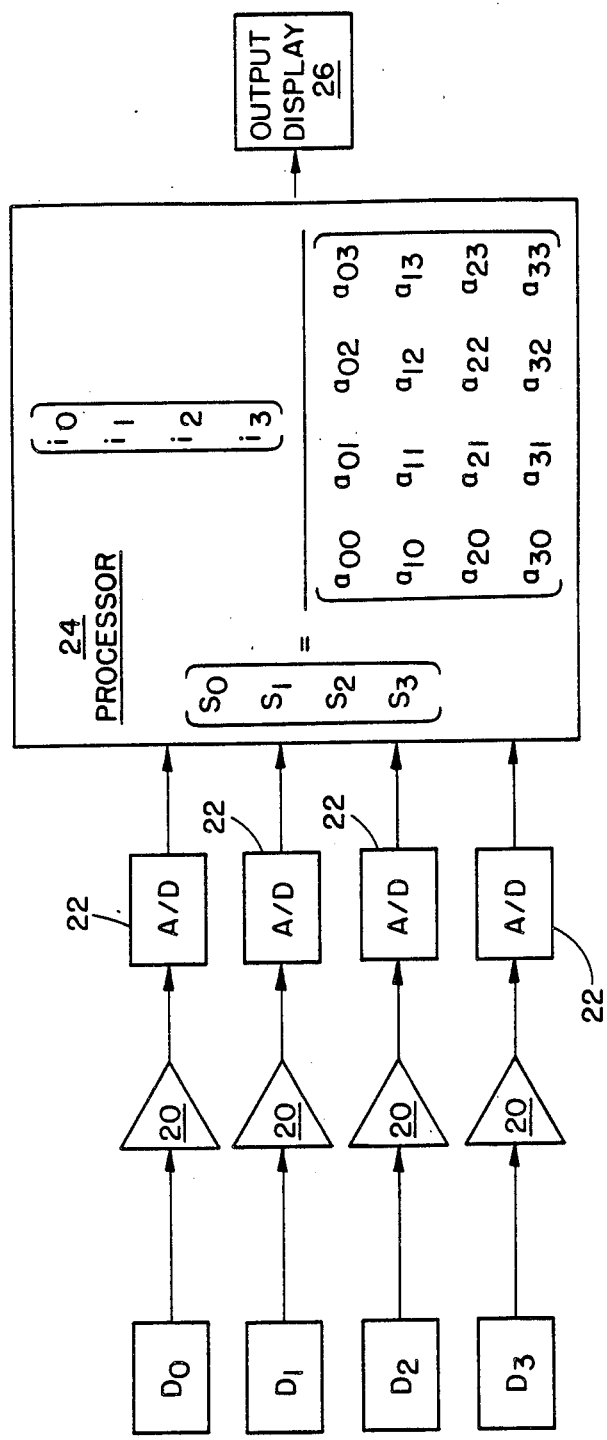
FIG. 2 illustrates an exemplary block diagram of a signal processing arrangement for processing the four photodetector output signals of FIG. 1.

FIG. 2 is a block diagram of an exemplary signal processing arrangement in which the output signals of photodetector $D_0$, $D_1$, $D_2$ and $D_3$ are initially amplified at 20, which affects the proportionality constant $k_n$ as described hereinabove, and are then converted to digital equivalent values by analog to digital converters 22 which are directed as inputs to a processor 24, preferably a microprocessor, which performs the calculation $\overline{S} = \overline{A}^{-1}\overline{I}$. In an alternative embodiment, the processor 24 may be equipped to handle the A/D conversions.

As shown in FIG. 2, the instrument of FIG. 1 can be readily interfaced to an on-line microcomputer 24 which receives as its input the digitized output electrical signals $i_0$, $i_1$, $i_2$ and $i_3$. The microcomputer stores the instrument matrix $\overline{A}$ in memory, determines its inverse, and calculates the four Stokes parameters using Eq. (6). The result can be displayed on a suitable output device 26. Alternatively, $\overline{A}^{-1}$ can be stored directly in the computer memory.

Although, the four Stokes parameters are a preferred and art recognized manner for describing the state of polarization of light, the instrument of FIG. 1 could be utilized to measure the state of polarization of light in other terms. Moreover, once the Stokes parameters are determined, other characteristics such as the coherency matrix can be determined and follow therefrom.

While several embodiments and variations of the present invention for a photodetector arrangement for measuring the state of polarization of light are described in detail herein, it should be apparent that the disclosure and teachings of the present invention will suggest many alternative designs to those skilled in the art.

What is claimed is:

1. A photopolarimeter for measuring the state of polarization of a light beam, comprising:
   a. a first photodetector, having a partially specularly reflecting surface on which the light beam is incident at an oblique angle with a first plane of incidence and is partially reflected therefrom, said first photodetector producing a first electrical output signal having a magnitude proportional to the radiation absorbed by the first photodetector;
   b. a second photodetector, having a partially specularly reflecting surface on which the light beam partially reflected from the first photodetector is incident at an oblique angle with a second plane of incidence, different from said first plane of incidence, and is partially reflected therefrom, said second photodetector producing a second electrical output signal having a magnitude proportional to the radiation absorbed by the second photodetector;
   c. a third photodetector, having a partially specularly reflecting surface on which the light beam partially reflected from the second photodetector is incident at an oblique angle with a third plane of incidence, different from said second plane of incidence, and is partially reflected therefrom, said third photodetector producing a third electrical output signal having a magnitude proportional to the radiation absorbed by the third photodetector; and
   d. a fourth photodetector having a substantially totally light absorptive surface on which the light beam partially reflected from the third photodetector is incident, said fourth photodetector producing a fourth electrical output signal having a magnitude proportional to the radiation absorbed by the fourth photodetector.

2. A photopolarimeter for measuring the state of polarization of a light beam as claimed in claim 1, including means, coupled to said first, second, third and fourth output signals, for simultaneously measuring all four Stokes parameters defining the state of polarization of a light beam.

3. A photopolarimeter for simultaneously measuring all four Stokes parameters defining the state of polarization of a light beam, as claimed in claim 2, further comprising means for converting each of said first, second, third and fourth output signals to a corresponding digital signal, and means, coupled to receive said corresponding digital signals, for calculating each of the four Stokes parameters pursuant to $\overline{S} = \overline{A}^{-1}\overline{I}$, wherein $\overline{A}$ is a four by four photopolarimeter matrix, and $\overline{I}$ is a four by one signal vector comprising said first, second, third and fourth output signals.

4. A photopolarimeter for simultaneously measuring all four Stokes parameters defining the state of polarization of a light beam, as claimed in claim 3, wherein said means for calculating comprises a microcomputer having the matrix $\overline{A}$ or $\overline{A}^{-1}$ stored therein.

5. A method for measuring the state of polarization of a light beam, comprising:
   a. directing the light beam onto a first photodetector, having a partially specularly reflecting surface, at an oblique angle with a first plane of incidence such that it is partially reflected therefrom, and producing with said first photodetector a first electrical output signal having a magnitude proportional to the radiation absorbed thereby;
   b. directing the light beam partially reflected from the first photodetector onto a second photodetector, having a partially specularly reflecting surface, at an oblique angle with a second plane of incidence, different from said first plane of incidence, such that it is partially reflected therefrom, and producing with said second photodetector a second electrical output signal having a magnitude proportional to the radiation absorbed thereby;
   c. directing the light beam partially reflected from the second photodetector onto a third photodetector having a partially specularly reflecting surface, at an oblique angle with a third plane of incidence, different from said second plane of incidence, such that it is partially reflected therefrom, and producing with said third photodetector a third electrical output signal having a magnitude proportional to the radiation absorbed thereby; and
   d. directing the light beam partially reflected from the third photodetector onto a fourth photodetector having a substantially totally light absorptive surface, and producing with said fourth photodetector a fourth electrical output signal having a magnitude proportional to the radiation absorbed thereby.

6. A method for measuring the state of polarization of a light beam, as claimed in claim 5, including the step of utilizing said first, second, third and fourth output signals to simultaneously measure all four Stokes parameters defining the state of polarization of a light beam.

7. A method for simultaneously measuring all four Stokes parameters defining the state of polarization of a light beam, as claimed in claim 6, further comprising the steps of determining $\bar{A}$, a four by four photopolarimeter matrix, converting each of said first, second, third, and fourth output signals to a corresponding digital signal, and calculating each of the four Stokes parameters pursuant to $\bar{S} = \bar{A}^{-1}\bar{I}$, wherein $\bar{A}$ is the four by four photopolarimeter matrix and $\bar{I}$ is a four by one signal vector comprising said first, second, third and fourth output signals.

8. A method for simultaneously measuring all four Stokes parameters defining the state of polarization of a light beam, as claimed in claim 7, said step of calculating including utilizing a microcomputer to perform the calculation $\bar{S} = \bar{A}^{-1}\bar{I}$, and storing $\bar{A}$ or $\bar{A}^{-1}$ in the memory of the microcomputer.

9. A method for simultaneously measuring all four Stokes parameters defining the state of polarization of a light beam, as claimed in claim 7, said step of determining $\bar{A}$, the four by four photopolarimeter matrix, includes determining $\bar{A}$ by calibrating the arrangement of the four photodetectors, including illuminating the photopolarimeter with input light that is polarized, sequentially, in four different linearly independent states, represented by four known linearly independent Stokes vectors, and recording the corresponding signal vector for each input state to determine $\bar{A}$.

10. A method for simultaneously measuring all four Stokes parameters defining the state of polarization of a light beam, as claimed in claim 7, said step of determining $\bar{A}$, the four by four photopolarimeter matrix, includes calculating $\bar{A}$ by utilizing the Mueller matrix $\bar{M}$ and the rotation matrix $\bar{R}$, wherein the Mueller matrix $\bar{M}$ is given by $$\bar{M} = r \begin{bmatrix} 1 & -\cos 2\psi & 0 & 0 \\ -\cos 2\psi & 1 & 0 & 0 \\ 0 & 0 & \sin 2\psi \cos\Delta & \sin 2\psi \sin\Delta \\ 0 & 0 & -\sin 2\psi \sin\Delta & \sin 2\psi \cos\Delta \end{bmatrix},$$

where r is the intensity reflectance for unpolarized (or circularly polarized incident light, and $\tan\psi \exp(j\Delta)$ is the ratio of the complex p and s reflection coefficients, and the rotation matrix $\bar{R}$ is given by $$\bar{R}(\alpha)) = \begin{bmatrix} 1 & 0 & 0 & 0 \\ 0 & \cos 2\alpha & \sin 2\alpha & 0 \\ 0 & -\sin 2\alpha & \cos 2\alpha & 0 \\ 0 & 0 & 0 & 1 \end{bmatrix},$$

to determine the individual elements $a_{mn}$ of the matrix $\bar{A}$.

* * * * *